United States Patent [19]

Andersen et al.

[11] Patent Number: 5,309,775
[45] Date of Patent: May 10, 1994

[54] APPARATUS FOR ANALYSIS OF SAMPLES OF FLUIDS

[75] Inventors: Joergen Andersen, Herlev; Kristian J. Hvidtfeldt, Virum; Ib O. Sinnerup, Humlebaek, all of Denmark

[73] Assignee: Radiometer A/S, Copenhagen, Denmark

[21] Appl. No.: 778,850

[22] PCT Filed: Jun. 13, 1990

[86] PCT No.: PCT/DK90/00147
 § 371 Date: Jan. 29, 1992
 § 102(e) Date: Jan. 29, 1992

[87] PCT Pub. No.: WO91/00520
 PCT Pub. Date: Jan. 10, 1991

[30] Foreign Application Priority Data

Jun. 23, 1989 [GB] United Kingdom ............... 8914456

[51] Int. Cl.⁵ ............................................. G01N 35/06
[52] U.S. Cl. ................................................. 73/864.22
[58] Field of Search ...................... 73/1 R, 1 G, 61.59, 73/64.56, 335.01, 864.21–864.25; 422/63, 64, 67, 68.1, 81, 82.01, 82.05; 436/11, 16, 50, 68, 43, 49, 54, 180; 220/669, 672, 675, 631, 604, 606, 707–709

[56] References Cited

U.S. PATENT DOCUMENTS

| | | |
|---|---|---|
| D. 325,257 | 4/1992 | Andersen et al. . |
| D. 325,258 | 4/1992 | Andersen et al. . |
| D. 325,259 | 4/1992 | Andersen et al. . |
| 3,290,920 | 12/1966 | Novak .................... 73/1 G |
| 3,690,833 | 9/1972 | Ferrari .................... 436/50 |
| 4,338,280 | 7/1982 | Ambers et al. ........... 73/864.22 |
| 4,604,263 | 8/1986 | Smernoff ................. 422/81 |
| 4,711,851 | 12/1987 | McNamara et al. ....... 422/63 |
| 4,844,871 | 7/1989 | Polaschegg ............... 436/68 |
| 4,889,255 | 12/1989 | Schiemann ............... 220/675 |
| 4,928,860 | 5/1990 | Knight ..................... 220/631 |
| 5,185,263 | 2/1993 | Kroneis et al. ............ 73/1 R |

*Primary Examiner*—Robert Raevis
*Attorney, Agent, or Firm*—Bryan Cave

[57] ABSTRACT

New apparatus for measuring parameters such as pH, $pCO_2$, $pO_2$, and Hb content of physiological fluids, especially blood, is described. The apparatus comprises novel means for suspending reagent vessels (34, 35, 40, 45, 50) having shoulders (51, 52) and containing calibrating solutions, rinsing solutions etc., as well as for suspending a liquid waste vessel (26) by suspending the vessels between rods (53, 54) fed to the analyser. The reagent vessels are provided with caps (55, 58) at the top and include liquid reagent conduit extending from the outlet aperture of the cap down into the liquid. When the vessel is mounted on the analyser a fixed inlet tube extending horizontally outwardly from the analyser penetrates a seal across the outlet aperture and connects with the liquid reagent conduit.

23 Claims, 4 Drawing Sheets

APPARATUS FOR ANALYSIS OF SAMPLES OF FLUIDS

The present invention relates to apparatus for carrying out analysis of fluids, usually physiological fluids, including gases and, usually, liquids such as blood, which comprises an analyser and a vessel for storing a reagent liquid used in the measurement.

In many instances it is very important to obtain reliable information about certain data about a blood sample from a patient as soon as possible in order to avoid an unnecessary delay in treating the patient in the most appropriate manner. The data desired may comprise any of the following:

Partial pressure of carbon dioxide in the blood sample—in the following referred to as $pCO_2$, partial pressure of oxygen in the blood sample—in the following referred to as $pO_2$, the pH-value of the blood sample, and the hemoglobin concentration of the blood sample, e.g. in percentage by weight—in the following referred to as Hb %.

When a correlated set of values for $pCO_2$, $pO_2$, pH, and Hb % is known, it is possible to determine a number of other parameters indicating the acid-base status of the blood sample, such as "buffer base", "base excess", "standard bicarbonate", "actual bicarbonate", "total $CO_2$". These terms are well known in the art. Their calculation is described in U.S. Pat. No. 3,654,445 and in Ole Siggaard-Andersen, The Acid-Base Status of the Blood, 4th edition, Munksgaard, Copenhagen 1976.

The parameters of the fluid which are measured are generally measured by electrochemical measuring devices, often including electrodes, for instance including a pH electrode, a $pCO_2$ electrode, and a $pO_2$ electrode, and may also comprise photometric sensing devices, for instance which are useful to determine the Hb level. These measurements invariably involve the transmission of electrical signals by the analyser, those electrical signals often being the direct results of the measuring process. It is necessary to take precautions to ensure that there is as little interference to those electrical signals as possible.

The measurements of the various parameters are carried out in a measurement section of the analyser. This section may comprise separate measurement chambers within which each measurement is carried out, for instance each of which contains a single electrode, or the measurements may be carried out in one or more chambers of which at least one contains two or more of the measuring devices or all of the measurements may be carried out in a single measuring chamber.

It is clearly important in such apparatus to ensure that after measurement of the parameters of a sample have been made, the sample inlet section and the measuring section of the analyser are rendered completely free of all traces of that sample, before the next sample is introduced for measurement. This is achieved by flushing a rinsing solution through the conduits of the analyser including the sample inlet section and the measuring section. The solution for carrying out the rinsing is generally supplied to the analyser from a separate vessel containing a store of the solution.

As well as rinsing the conduits of the analyser between samples, it is also necessary periodically to calibrate the apparatus to ensure accuracy of the readings being obtained. The calibration is carried out by introducing into the measurement section standard calibrating solutions having known values for the respective parameter or parameters. As for the rinsing solution, it is convenient for a store of the calibrating solutions to be carried in storage vessels co-operating with the conduits of the analyser.

Where the analyser includes a pH electrode, as is normal, this is usually associated with a reference, calomel electrode. A salt bridge is formed between the reference electrode and the glass electrode of the pH measuring system. This salt bridge usually comprises potassium chloride solution. It is usual to maintain a store of potassium chloride solution associated with the analyser.

Apparatus of this type also includes a waste outlet through which all of the waste liquid is disposed of. Thus the liquid samples are ejected after measurement, the used rinse solution is ejected after rinsing and the calibrating solutions are ejected after the calibrating process out of the waste outlet. In order to avoid waste liquids coming into contact with the analyser, it is preferred for the waste outlet to direct liquid into a special waste vessel.

There are many liquids associated with an analyser of this type, some of which are electrolytes. From a user's point of view it is important that the liquid storage vessels be easily connected to and disconnected from the analyser. Further, to avoid interference with the electrical signal transmissions, it is important to keep the liquids from escaping from their respective conduits, and in particular to keep the external parts of the apparatus free of liquid, especially around the regions of the apparatus where the storage vessels for the various liquids are retained and where the inlets to the analyser for those liquids are positioned and in the region of the waste outlet and waste vessel.

In our existing system, the Acid Base Laboratory ABL4, the storage vessels for the calibrating solutions are arranged for gravity feed by being supported on the analyser above the measuring section, with the bottle openings directed downwards and connected to fittings on the analyser. The rinse solution vessel, the waste bottle, and the potassium chloride vessel are each supported in a basket affixed to the analyser underneath the calibrating solution bottles. To mount a calibrating solution bottle onto the analyser the cap with which it is supplied first has to be removed. Then a stopper is fitted into the neck of the bottle and the stopper pushed into the dispenser in the analyser. When replacing an empty bottle with a new bottle, the old bottle with its plastic stopper is removed from the analyser and the plastic stopper is switched to the new bottle which is then positioned in the dispenser. It is necessary first to remove any solutions remaining in the dispenser wells, for instance using a syringe. With this system it can be difficult to avoid spillage of liquid and changeover can be inconvenient and can take an undesirable length of time.

To mount a rinse solution bottle, a proteolytic enzyme pellet has to be manually placed into a fresh bottle of base solution. After complete dissolution a mounting lid attached to a rinse inlet pipe is fitted onto the bottle of rinse solution which is then positioned in the basket. It is difficult to avoid spillage of the solution when the mounting lid and associated pipe is removed from an exhausted bottle. Replacement of the potassium chloride solution bottle is carried out in a similar manner to the rinse solution bottle.

In the Ciba-Corning 278 Blood Gas System the two calibrating solution bottles and the rinse solution bottle are mounted in a cavity formed in the front of the analyser cabinet with their mouths pointing downwards. They are supplied with caps secured to the mouths of the bottles and which are not removed before use. The caps comprise a central seal section which is penetrated by a penetrating member on a lever fixed to the analyser which is moved upwards to engage the bottle when in position in its cavity in the analyser. This system still suffers the problem that it is difficult to prevent escape of liquid from the inverted bottles when they are being replaced. Furthermore providing the penetrating member on a lever attached to the analyser requires the pipes within the analyser to be movable, which can be inconvenient.

New apparatus according to the invention comprises an analyser for conducting measurements of properties of samples of physiological fluids involving transmission of electrical signals by the analyser, and a reagent liquid storage vessel mountable on the analyser, in which the analyser comprises sample inlet section and measuring section, and means for directing a flow of reagent liquid from the reagent liquid storage vessel and through the measurement section after discharge of sample therefrom and in which the directing means comprise reagent liquid input mechanism for directing a flow of reagent liquid from the storage vessel to the measurement section and the analyser has support means capable of supporting the liquid storage vessel in position for co-operation with reagent liquid input mechanism and the analyser has pump means for pumping reagent liquid from the storage vessel to the measurement section, characterised in that the storage vessel has a sealed outlet aperture, the support means are suitable for suspending the storage vessel with the outlet aperture at the top of the vessel, and the storage vessel has an internal liquid conduit extending from the aperture into the liquid near to the bottom of the vessel (the vessel is mounted on the analyser) and the input mechanism of the apparatus comprises an open ended tube fixed with respect to the analyser and extending from the analyser which is capable of penetrating the aperture seal as the storage vessel is mounted on the analyser and of communicating with said liquid conduit inside the storage vessel (when the vessel is mounted on the analyser) thereby providing a continuous channel for liquid from the vessel to the measurement section.

Usually the apparatus comprises electrochemical measuring devices, such as a pH electrode, a $pCO_2$ electrode, and/or a $pO_2$ electrode, and/or ion selective electrodes such as potassium or sodium electrodes. The apparatus may alternatively, or additionally contain photometric sensing devices, for instance for measuring Hb levels of blood or other fluids. Usually the apparatus is a pH/blood gas analyser, and may additionally or alternatively be a physiological gas, or breath, analyser and/or may be suitable for analysing urine, plasma, or other physiological liquids or gases.

Usually the apparatus comprises a plurality of liquid storage vessels of the type defined and the analyser has separate reagent inlet means for each liquid and separate support means for each vessel. The reagent liquids may for instance comprise calibrating solutions for any of the electrodes. For a blood gas analyser it is generally preferred to have two such calibrating solutions which can have accurately controlled pH levels. It is convenient for rinsing solution to be provided in the specified reagent vessel. When the reagent is rinsing solution, the analyser comprises means for directing the rinsing solution from the vessel into the respective reagent input mechanism and thence to the sample inlet section and measurement section.

In the apparatus there is preferably means for discharging any fluids from the measurement chamber and depositing the liquids into a removable liquid waste vessel, and the analyser has support means for suspending the waste vessel.

In the invention the or each reagent vessel and waste vessel as described above, if present, when in position for use is supported such that presence of liquid between the outside of the respective vessel and the analyser is minimised by providing a protrusion of one or both of the adjacent vessel and analyser surfaces which maintains a distance between those surfaces sufficient to prevent capillary formation. The distance is generally at least 0.5 mm, preferably at least 1 mm. The distance is generally less than 5 mm to minimise wastage of space, and is conveniently around 2 mm. Although the protrusions may be formed on the apparatus, it is more convenient for the protrusions to be formed on the surface of the respective vessel, for instance by moulding.

In the apparatus it is preferable for the or each of the reagent vessels and the described waste container, if present, to fit into one or more cavities in the analyser, so that the back and bottom and optionally sides and top of the or each vessel are surrounded, and the presence of liquid on the lowermost surface of the cavity is minimised by constructing the lowermost surface of the analyser cavity so that it inclines to the horizontal downwards towards the opening of the cavity such that liquid will run off the surface. Usually the reagent vessel or waste vessel is shaped to correspond to the shape of the cavity, i.e. has an inclined lower surface, in order to maximise the internal volume of the vessel.

The support means for suspending the vessels generally comprise a pair of rods which are parallel with one another in a horizontal plane, and which are secured to the analyser such that they extend outwardly from it and the vessel has co-operating means on its two sides for co-operation with the rods, the co-operating means comprising a shoulder at the top of each side, each of which rests on one of the rods when the vessel is supported on the analyser. It may be possible to provide the shoulder along a portion only of either or both sides although it is convenient for the shoulder to extend along substantially the entire length of each side. In the preferred apparatus comprising a plurality of vessels each with support means, it is convenient for the vessels to be supported adjacent one another with opposing shoulders at the same height so that a single rod between adjacent vessels can support both vessels by co-operating with those shoulders.

When a plurality of vessels are provided adjacent one another, it is generally convenient for them to be shaped such that the vessels are narrower side to side at one region of the front face such that an operative's fingers can reach between the vessels and grab the sides of the vessel for withdrawing it from the analyser. The entire vessel may be narrower than the distance between the extent of the shoulders to provide the required shaping. Alternatively the shoulder may be the upper edge of a groove formed in the side of the vessel so that the width of the vessel is the same as the width between the extent of the shoulder over most of the vessel, the shaping being provided in the form of indentations in the sides at the appropriate positions.

The vessel or vessels in the preferred embodiment are mounted and removed from the analyser by motion along a substantially horizontal path. The tube of the analyser's input mechanism is fixed in such apparatus to extend substantially horizontally from the analyser, i.e. parallel to the support rods. The outlet aperture of the reagent vessel is thus conveniently arranged to be in substantially vertical plane as the vessel is mounted on the analyser.

In the invention there is also provided a new reagent vessel containing a liquid reagent, which is suitable for use as part of the new apparatus. The vessel comprises a bottle with a cap permanently fixed by a fluid tight fixture to the bottle opening, the cap comprising a cavity having a sealed outlet aperture capable of being broken by the inlet tube of the input mechanism of the analyser, and in which the cavity comprises also an inlet aperture in fluid communication with a reagent liquid conduit which extends into the liquid.

In the vessel the cap is formed such that the input mechanism of the analyser is capable of forming a fluid tight communication with the inlet aperture by the provision of a gasket in the cap which seals the connection between the analyser inlet tube and the liquid conduit in the vessel.

The seal of the cap is generally formed from a gas and vapour impermeable material, usually comprising a laminate including metal foil.

The new reagent vessel may be for providing the rinsing solution. In one embodiment it is supplied with a base solution contained in the bottle and a proteolytic enzyme in the form of a dry composition isolated from the solution in a form such that the enzyme can be contacted with the base solution and dissolved in it to form the rinsing solution. An enzyme generally needs to be isolated from the solution and from the atmosphere during storage to prevent loss of activity. Isolation may be by providing the enzyme in a second cavity in the cap of the vessel, and providing means in the cap to break the seal between the second cavity and internal space of the bottle to release the enzyme into the base solution. The means may for instance be provided in the form of a plunger within the cavity, one end of which can be depressed from outside the vessel and the other end of which is provided with a member which penetrates the seal when the plunger is depressed, and which pushes the enzyme from its cavity into the vessel. The rinse solutions may for instance comprise the components described in DE-A-3006769.

The vessel may alternatively contain pH calibrating solution for the measuring instruments. The calibrating solutions may be of the conventional types and are for instance as described in any of the earlier descriptions of calibrating solutions described in WO-A-8804426.

Further according to the invention there is provided a waste vessel suitable for use in apparatus according to the invention comprising a bottle and a cap permanently attached to the bottle opening, the cap having an aperture, means for selectively opening and closing the aperture and means for co-operating with the waste outlet of the analyser such that waste liquid directed through the analyser waste outlet enters the waste vessel through the opened aperture. It is useful to be able to close the aperture for disposal of the waste. Usually the means for opening and closing comprises a pair of plates each having an aperture, one of which is fixed relative to the vessel and the other of which is rotatable between an open position where the plates' apertures are aligned and a closed position where the rotatable plate occludes the aperture in the fixed plate and thereby closes the bottle opening. Alternative methods of closing an aperture on the cap, such as using a sliding plate, are possible.

Usually the waste outlet of the analyser comprises a pipe extending substantially vertically downwards from the analyser, and the waste vessel cap is arranged for cooperation with such an outlet, preferably without requiring vertical movement of either the waste outlet or the waste vessel or the provision of a separate funnel for directing liquid waste from the outlet into the vessel.

The internal part of the analyser may be substantially as in our present ABL analyser.

The apparatus of the invention is much more convenient to use than existing apparatus of the type and furthermore avoids liquid spillage and more particularly avoids liquid standing on the analyser and contacting other components, especially the reagent vessels, thereby minimising interference of the electrical signals of the analyser.

The invention will be better understood by reference to the following drawings of a preferred embodiment of the invention, in which.

Figure 1:
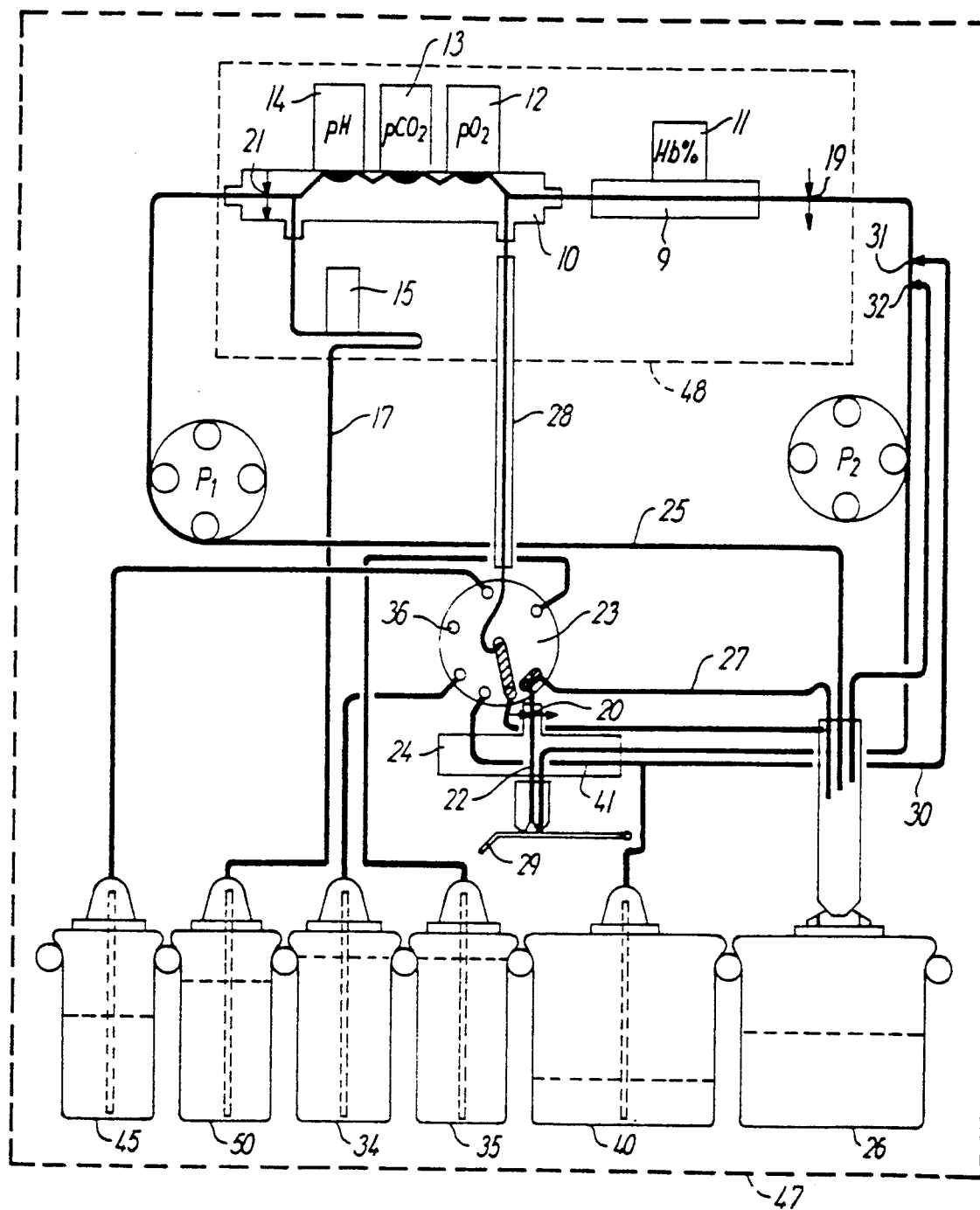
FIG. 1 is a schematic layout of the apparatus.

The presently preferred embodiment of the automatic blood sample analyser according to the invention is adapted for directly measuring and displaying the measured values of the blood parameters pH, $pCO_2$, $pO_2$, and Hb %. Thus, the fluid conduit system of the analyser shown in FIG. 1 includes a measuring section 10. Said measuring section is provided with three measuring chambers, viz. one for each of the blood parameters pH, $pCO_2$, and $pO_2$. A photometric hemoglobin measuring device 11 is arranged at the separate Hb % measuring section 9, and the other measuring chambers are provided with measuring electrodes 12-14 of a type wellknown in the art, or other measuring devices being able to convert the measured parameter values into electrical currents or signals. A calomel electrode or reference electrode 15 for the electrode 14 is connected to a container or source 50 for a solution of KCl and to the measuring section 10 with the pH-electrode by means of a conduit 17. Solutions of KCl may be passed from the container 50, through the conduit 17 to the calomel electrode 15 and further to the end portion of the measuring section 10 by means of a liquid transporting device.

It should be understood that it is possible to provide the analyser with measuring devices of other types than those used in the embodiment described. If desired, the analyser may also be adapted for measuring another number of and/or other types of parameters, and one or more measuring devices may be arranged in a single chamber.

The conduit system of the analyser embodiment shown in FIG. 1 also comprises an inlet section 22 connected to the measuring sections 9 and 10 via Flachhahn valve 23.

The blood sample analyser shown in FIG. 1 also comprises storage vessels 34, 35 for two different pH calibrating fluids of known composition. In principle these fluids may be of any type provided that the pH-values thereof are known or may be currently calculated.

Gas electrode calibration gas mixtures may currently be supplied to the analyser through gas calibration supply part 36 of valve 23. The gas supply part is connected to a gas mixer supplying the analyser with several calibration gas mixtures.

A rinsing fluid storage container or reservoir 40 is connected to the measuring section 10 by means of a rinsing fluid conduit 41. A cleaning fluid storage container 45 is also connected to the measuring system via the valve 23. This fluid is used regularly, e.g. daily to clean the internal conduits of the apparatus.

The analyser furthermore comprises pumps $P_1$, $P_2$ or other fluid transporting devices for moving fluids in the conduit system. In FIG. 1 the dotted line 47 indicates the outer limits of the analyser cabinet, and the dotted line 48 indicates an area or space in which the temperature is controlled so as to be maintained at a substantially constant value, preferably at 37° C.

In principle the blood analyser disclosed functions as follows:

If the analyser is ready for use, which means that no calibrating or rinsing operations are being performed, the inlet key 29 may be opened. The valve 23 is actuated. A blood sample to be measured is now introduced into the inlet section 22 situated in a first preheater 24. Preferably, the blood sample to be measured is present in a syringe, and the blood sample may then be forced into the inlet section 22 by depressing the piston of the syringe when the outlet end of the syringe cylinder has been pressed against the analyser inlet. If desired, the blood sample may alternatively be sucked into the inlet section 22 or introduced by means of an automatically operating sampler. When the blood sample introduced into the inlet section has reached the liquid sensor 20, the amount of blood introduced is sufficient, and a possible excessive amount will flow through the drainage conduit section 27 to the waste container 26. When the sensor 20 has detected that the blood sample has arrived to that position and the inlet key 29 has been closed, the pump $P_1$ starts operating for pumping KCl solution from the container 50 through the conduit 17 to the end portion of the measuring section 10. Then both the pumps $P_1$ and $P_2$ are operated so that the blood sample is being pumped from the valve 23 via a second preheater 28 into the measuring sections 9 and 10 with the various measuring chambers. The operation of the pumps $P_1$ and $P_2$ is stopped, when the liquid sensors 19 and 21 detect that the blood columns sucked into the measuring sections have reached the position of those sensors.

When the measuring operation has been terminated, the blood sample is discharged into the waste container 26 by means of the pumps $P_1$ and $P_2$. Thereafter a rinsing liquid is pumped from the container 40 through the conduit 30 via valve 31 to the Hb % measuring section 9 and through the conduit 41 and the valve 23 to the measuring section 10. The rinsing liquid is then pumped through the drainage conduit 25 to the waste container 26. In order to obtain an effective of the conduit system it is preferably flushed alternatively with rinsing liquid from the container 40 and with atmospheric air drawn into the system via valves 23 and 32.

The analyser is preferably self-calibrating. The calibrating procedure may start automatically at regular time intervals, for example of half an hour. The analyser is, however, preferably programmed so that it does not interrupt a measuring procedure in order to start a scheduled calibrating procedure, but postpones the calibration till the measuring procedure has been terminated. Additionally, the analyser should preferably automatically perform self-calibration as soon as the analyser is energized after a preceding interruption of current supply to the analyser.

The initial steps of the pH calibration procedure comprise pumping of calibrating liquid from one of the containers 34 and 35 via the valve 23 through the measuring section 10 in order to remove possible residues of previously used rinsing fluids, and thereafter a fresh amount of the same calibrating liquid is passed into the measuring section 10, and first calibrating measurements are being made by the measuring device 14 similar to the measurements performed on the blood sample. The first calibrating liquid is then discharged from the measuring section into the waste container 26 by means of the pump $P_1$, and the measuring section 10 is thereafter flushed with a second calibrating liquid from the other of the containers 34 and 35, whereafter similar calibration measurements of the second calibrating liquid are being performed. The results of the calibrating measurements are being transmitted to and stored in a calculator or computer which is adapted to evaluate the results received from the measuring device 14 when measuring blood samples, on the basis of the latest calibration results as will be described in the following. When the measurements of the second calibrating liquid have been terminated, the said liquid is discharged from the apparatus and the measuring devices 12 and 13 are calibrated by passing a calibrating gas into measuring section 10 and making calibrating measurements on the gas. The calibration gas is a mixture of pure $CO_2$ and ambient atmospheric air and comprises 5.6% $CO_2$. Less frequently, for example once a day, the $pO_2$ electrode is calibrated on pure $CO_2$ and the $pCO_2$ electrode is calibrated on a gas mixture comprising 11.2% $CO_2$ After completion of the calibration on the 5.6% $CO_2$ gas the analyser is again ready to receive a blood sample.

Figure 2:
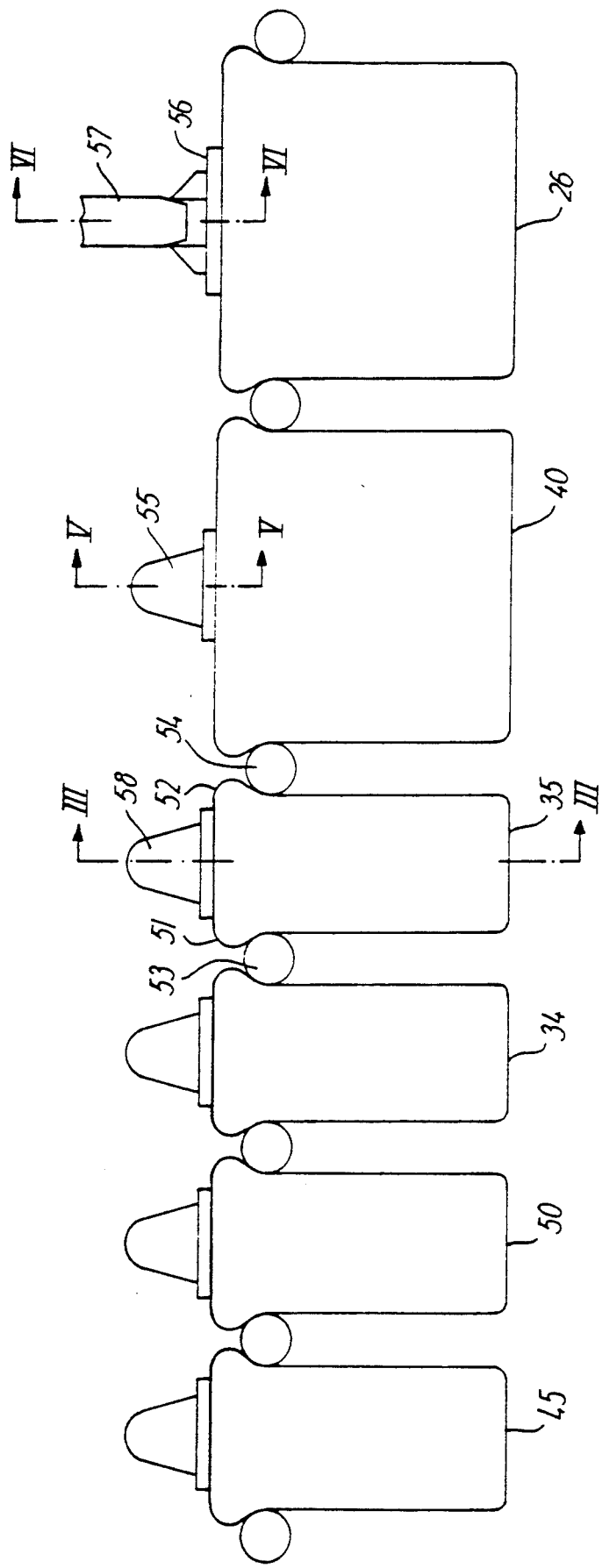
FIG. 2 shows a view from the front of the apparatus showing the reagent vessels supported on the analyser.

The method by which the storage vessels for calibration solution, 34 and 35, the storage vessel for rinse solution 40, the waste vessel 26, the cleaning solution vessel 45, and the potassium chloride vessel 50 are supported on the analyser is shown more clearly in FIG. 2. As can be seen, each vessel has a shoulder on each side. These shoulders are represented as reference numerals 51 and 52 on vessel 35. This allows the vessels to be supported between a pair of rods, 53 and 54, respectively, which extend substantially horizontally from the analyser. As can be seen, the diameter of the rods and the width of the shoulders are chosen so that one rod supports the shoulders of adjacent vessels. For instance rod 53 supports the shoulders of vessels 34 and 35. In this way, the space taken up by the vessels can be minimised. The vessels are removed from and replaced on the analyser by sliding the shoulders along the rods. The vessels thus move along a substantially horizontal path at a predetermined height to the desired position. Each of the vessels 34, 35, 40, 45, and 50 has a cap, 55, 58 which has a seal in its vertical face pointing towards the analyser which is penetrated by the horizontal piercing member being part of the inlet mechanism of the analyser.

The waste vessel 26 has a cap 56 having an aperture in its top which is directly below the waste outlet 57 in use. The construction of the cap is shown more clearly in FIG. 6.

Vessels 26, 34, 35, 40, 45, and 50 are usually made of a moulded plastics material which is transparent or translucent so that the level of liquid within the vessels can be checked by an operator.

Figure 3:
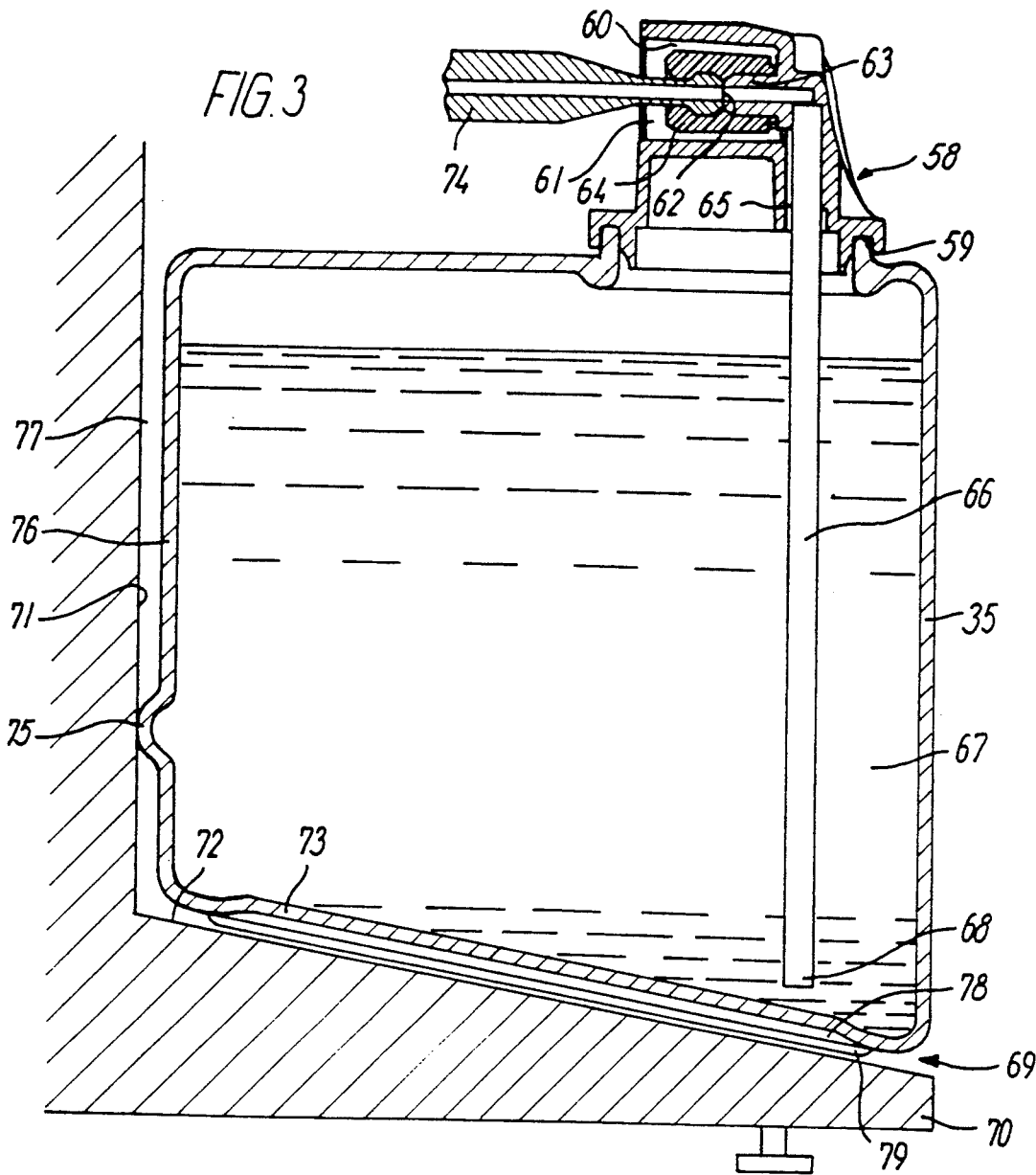
FIG. 3 is a cross-section along line III—III of FIG. 2 through one of the storage vessels for calibrating solution.

Referring now to FIG. 3 there is shown a section through line III—III in FIG. 2 of the calibrating solution vessel 35. The vessel has a cap 58 which is welded onto the top of the bottle at 59. The cap 58 has a cavity 60 having an outlet aperture 61 and inlet aperture 62. The vessel is supplied with a membrane sealing the outlet aperture 61. The inlet aperture 62 is formed in a tube 63 extending into the cavity 60. This tube is surrounded by an annular gasket 64 which extends beyond the tip of the tube 63. The bore of tube 63 extends through the back of the cavity 60 and into a second cavity 65 in which is held a tube 66 which extends down into the liquid 67 in the vessel, its end 68 being near to the bottom of the vessel.

The vessel fits into a cavity 69 of the analyser 70, which has a substantially vertical wall 71 and a sloping base surface 72 which allows runoff of any liquid. The vessel 35 is shaped to correspond to the cavity 69, and thus has a sloping lower wall 73. When the vessel is in position for use, as shown in FIG. 3, the horizontally directed piercing member 74 has penetrated the membrane sealing the outlet aperture 61 to enter the cavity 60 and form a fluid tight seal with gasket 64. There is then formed a continuous fluid conduit to allow passage of liquid 67 through the tube 66, via aperture 62 and into the inlet mechanism of the analyser via the bore of member 74. The position of the vessel with respect to the analyser 70 is determined in part by the communication of the member 74 with the vessel inlet aperture 62, and partly by the abutment Of the walls Of the vessel with the walls of the cavity 69 in the analyser. A protrusion 75 is molded in the back face 76 of the vessel, which serves to determine the position of the vessel with respect to the analyser. This protrusion has the additional function of maintaining a gap 77 between the wall 76 of the vessel and the vertical wall of the cavity, so that a capillary cannot be formed between the walls, to eliminate any electrically conducting reagent layers between the analyser and the vessel which might otherwise lead to electrical currents interfering with the electrical signals obtained with the measuring devices and thus to incorrect analysis results.

Furthermore a distance is also maintained between the bottom surface 73 of the vessel and the bottom wall 72 of the analyser cavity by providing an indentation 78 in the bottom wall of the vessel as well as by providing ridges 79 down each side of the wall. This again prevents capillary formation between the two surfaces and any liquid runs off down the slope.

The vessels shown in FIG. 2 are suspended from the rods extending into the cavity of the analyser by the provision of shoulders, as has been described above. The distance between the sides of the vessels shown in FIG. 2 aside from the shoulders formed at the tops of the sides, is substantially constant. The distance between the sides of adjacent vessels below the shoulders is sufficient for an operators fingers to be able to grab the sides of the bottle to withdraw it from the analyser.

Figure 4A:
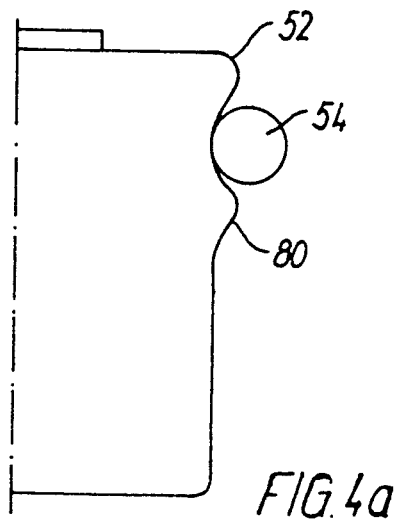
FIGS. 4a and 4b show partial front views of two alternative profiles of storage vessels.

Alternative bottle profiles may be used which enable the vessels to be suspended from the same rods. Examples of alternative profiles are shown in FIGS. 4a and b. The vessel shown in FIG. 4a has a shoulder 52 as well as a ridge 80 lower down the side. The ridge 80 ensures that the vessel is slid onto the analyser at exactly the right height and direction for registration of the cap of the vessel with the inlet mechanism of the analyser.

Figure 4B:
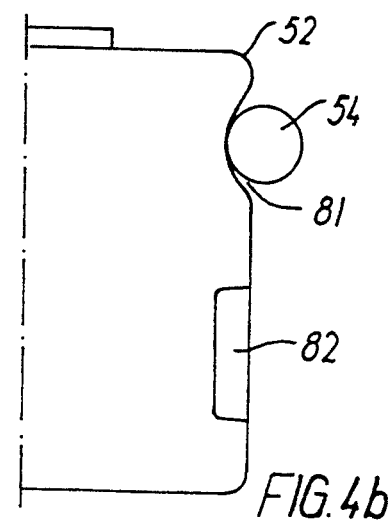

A further profile is shown in FIG. 4b, in which the shoulder is formed as the upper surface of a groove 81 formed in the side of the vessel. This has the same advantages with respect to ensuring the vessel is correctly positioned as the embodiment shown in FIG. 4a. It is the further advantage that the width of the vessel is maximised between the top and the bottom which maximises the capacity of the vessel. With this embodiment the side walls of adjacent vessels may be too close to one another for the vessels to be grabbed for removal. It is therefore preferred to provide indentations 82 on each side of the vessel as finger holes.

Figure 5:
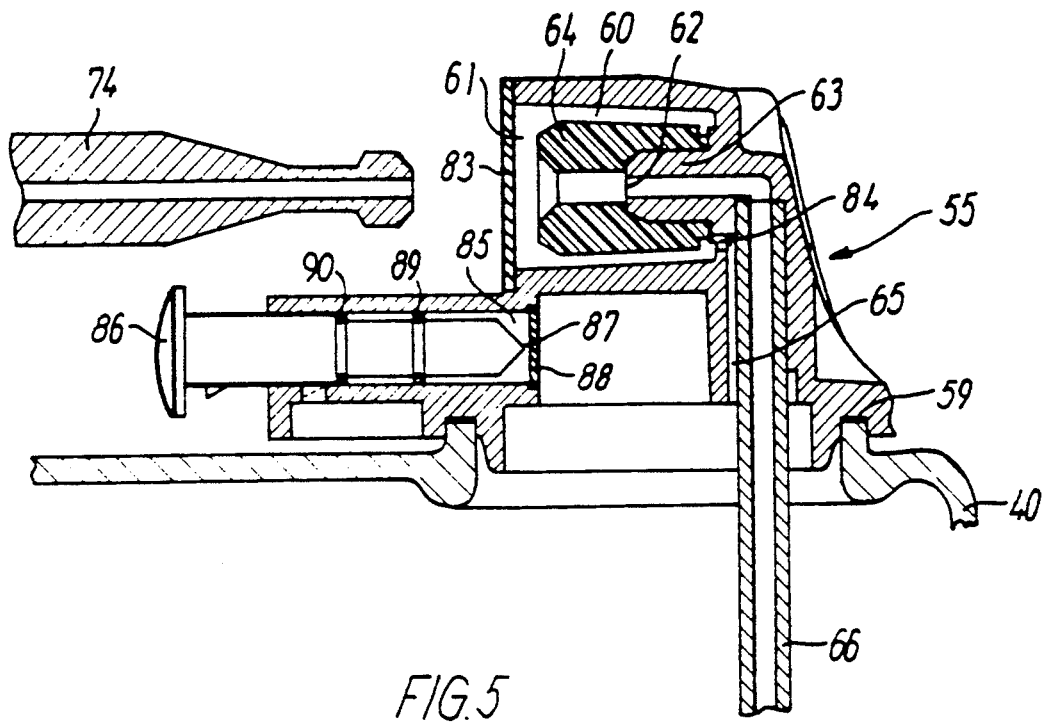
FIG. 5 is a cross-section along line V—V of FIG. 2 through the cap of a rinsing solution vessel.

FIG. 5 shows a cross-section along line V—V in FIG. 2 of a rinse bottle prior to being received on an analyser. A cap 55 is mounted on the vessel 40 by welding at 59. The cap comprises a cavity 60 which has an outlet aperture 61 sealed by a foil 83 which is vapour impermeable. An inlet aperture 62 is formed in a tube 63 extending into the cavity and whose other end opens into a second cavity 65 into which is fitted a tube 66 which extends downwards into the base solution for forming the rinsing solution in the vessel. The cavity 60 includes an annular gasket 64 which forms a fluid tight fitting around the tube 63. A small hole 84 between the first cavity 60 and the second cavity 65 allows ingress of air into the second cavity 65 and thence into the vessel from the outside via aperture 61 and cavity 60 when the vessel is mounted on the analyser, as liquid is removed from the vessel. In FIG. 5 there is also indicated the piercing member 74 of the inlet mechanism of the analyser, immediately prior to piercing of the foil seal 83.

The cap 55 of the rinse solution vessel comprises a third cavity 85 in which is received a plunger 86 which has a pointed end 87. When the plunger 86 is depressed the end 87 penetrates the thin wall 88 of the third cavity 85 to form a fluid conduit from the third cavity into the inside of the vessel. A dried enzyme preparation is positioned within the cavity 85 adjacent the wall 88, so that it is dropped into the solution when the plunger 86 is depressed. The plunger has seals 89 and 90 to form a fluid tight seal within the cavity 85 to prevent liquid escaping from the vessel through cavity 85. Generally the enzyme preparation is released into the base solution a few hours prior to use to ensure complete dissolution of the enzyme to form the desired rinse solution.

Figure 6:
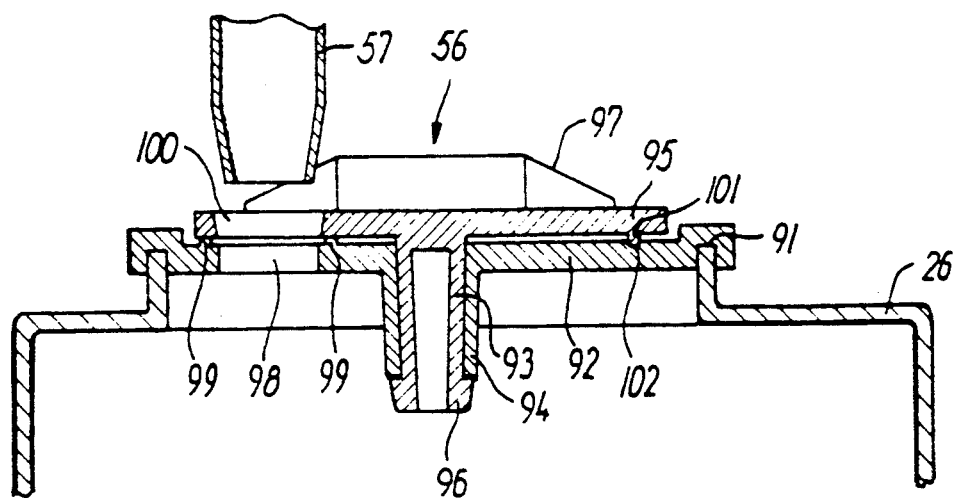
FIG. 6 is a cross-section along line VI—VI of FIG. 2 through the cap of a waste vessel.

FIG. 6 is a section along line VI—VI of FIG. 2 through the cap of a waste vessel. Vessel 26 comprises a cap 56 fixed to the vessel by welding at 91. The cap comprises a bottom plate 92 which has a central aperture 93 surrounded by a flange 94, as well as a top plate 95 having a snap fitting 96 depending from its centre which fits through the aperture 93 and is locked in position to allow relative rotational movement between the plates. The plate 95 has upwardly extending ridges 97 which can be gripped to rotate the top plate.

Lower plate 92 has an aperture 98 which is surrounded on the upper surface of the plate by a circular ridge 99 molded into the plate. The upper plate has an aperture 100 which, when the cap is in the open position as indicated, is located immediately above the aperture 98. The circular ridge 99 contacts the lower face of the plate 95 to form a substantially fluid tight seal between the plates. The plates are held in the open position by the reception of a pin 101 on the upper plate in a socket 102 on the lower plate.

In the closed position, not shown in the diagram, the upper plate is rotated so that the aperture 100 is no longer positioned above the aperture 98, but so that a region of the upper plate occludes the aperture 98 and so that a fluid tight seal is formed by contact of the ridge 99 with the lower side of the plate 92. The plates may be secured in the closed position by the pin 101 being received in a different socket which is positioned at an appropriate point in the upper surface of the lower plate 92.

When in use, as shown in FIG. 6, the aligned apertures 98 and 100 are positioned vertically below the waste outlet 57 of the analyser so that any waste liquid discharged therefrom flows through the apertures and into the waste vessel.

The following examples give details of the recipes for the various reagent liquids.

EXAMPLES

Calibrating Solution pH 7.400

A calibrating solution having a pH of 7.400±0.005 at 37° C. and which has a sodium ion concentration of 160.8±3 mmol/l and a chloride ion concentration of 106.2±1 mmol/l at 20° C. is formed with the following ingredients:

| Sodium hydrogen carbonate | 0.0226 g |
|---|---|
| HEPES | 23.7191 g |
| Sodium hydroxide | 2.1504 g |
| Kathon 886 | 0.060 g |
| Triton CF10 | 0.050 g |
| Deionised water to | 1,000 g |

Calibrating Solution pH 6.800

A calibrating solution having a pH of 6.800±0.005 at 37° C. and having a sodium ion concentration of 106.8±3 mmol/l and a chloride ion concentration of 118.4±1 mmol/l at 20° C. contains the following ingredients:

| Kathon 886 | 0.060 g |
|---|---|
| Triton CF10 | 0.050 g |
| Sodium chloride | 6.8505 g |
| MOPS | 20.8764 g |
| Sodium hydroxide | 1.6782 g |
| Deionised water to | 1,000 g |

Rinse Solution

A base solution is made up of the following components:

| Potassium chloride | 3.728 g |
|---|---|
| Sodium chloride | 2.922 g |
| Sodium hydrogen carbonate | 0.0303 g |
| Kathon 886 | 0.060 g |
| Triton CF10 | 0.050 g |
| Deionised water to | 1,000 g |

The base solution contains sodium ions in a concentration of 50.5±1.0 mmol/l, potassium ions in an amount 50.2±1.0 mmol/l and chloride ions in an amount of 100.3±1.6 mmol/l at 20° C. The solution has a pH of 7.35±0.35. To form the rinse solution subtilisin enzyme is added to the base solution in an amount of 20 mg per 1000 g base solution.

Salt Bridge Solution

A salt bridge solution for the calomel electrode of the pH measuring part of the apparatus is formed from the following components:

| Potassium chloride | 220 g |
|---|---|
| Triton X100 | 0.43 g |
| Kathon 886 | 0.06 g |
| Deionised water to | 1,000 g |

The solution contains potassium chloride in the amount of 2.951±0.040 mmol/kg of water.

Cleaning Solution

A cleaning solution for regular (e.g. daily) cleaning of the measuring part of the apparatus by being injected via the sample injection means, comprises 200 g Deconex (trademark) (tenside mixture) made up to 1,000 g with deionised water.

We claim:

1. Apparatus comprising an analyzer for conducting measurements of properties of samples of physiological fluids involving transmission of electrical signals by the analyzer, and a reagent liquid storage vessel mountable on the analyzer, said analyzer comprising a fluid conduit system comprising a sample inlet section, a measuring section positioned downstream of the inlet section, a reagent liquid conduit, and means for directing a flow of reagent liquid from the reagent liquid storage vessel and through the measurement section after discharge of a sample therefrom, said directing means comprising a reagent liquid input mechanism for directing a flow of reagent liquid from the storage vessel through the reagent liquid conduit to the measurement section, said analyzer further comprising support means capable of supporting the liquid storage vessel in position for co-operation with said reagent liquid input mechanism, and pump means arranged in the fluid conduit system for pumping reagent liquid from the storage vessel to the measurement section, said storage vessel having a sealed laterally facing outlet aperture, the support means supporting the storage vessel in position for use with the laterally facing outlet aperture toward the top of the vessel and positioned relative to the input mechanism for aligning said input mechanism with said laterally facing outlet aperture, said storage vessel having an internal liquid conduit extending from the aperture into the liquid near to the bottom of the vessel, said input mechanism of the apparatus comprising an open ended tube fixed with respect to the analyzer and extending from the analyzer for penetrating the aperture seal of the laterally facing outlet aperture as the storage vessel is mounted on the analyzer and for communicating with said liquid conduit inside the storage vessel, the reagent liquid conduit of the analyzer, the open ended tube and the liquid conduit of the vessel thereby providing a continuous channel for liquid from the vessel to the measurement section.

2. Apparatus according to claim 1 further comprising a plurality of said reagent liquid storage vessels, and said analyzer having support means and separate reagent inlet means for each of said reagent liquid storage vessels.

3. Apparatus according to claim 2, wherein the support means for supporting each vessel comprise a plurality of rods which are parallel with one another and at substantially the same height and which are secured to the analyzer such that they extend outwardly from the analyzer, the vessels having co-operating means on their two sides for co-operation with the rods, the co-operating means comprising shoulders at the top of each side of the vessels, the rods being arranged such that the vessels may be supported adjacent one another with opposing adjacent shoulders at the same height and so that a single rod between two adjacent vessels can support the two adjacent vessels by cooperating with opposing adjacent shoulders on the two adjacent vessels.

4. Apparatus according to claim 1 wherein said reagent liquid storage vessel contains a calibrating solution for the analyzer.

5. Apparatus according to claim 1 wherein said liquid reagent storage vessel contains a rinsing solution, and in which the analyzer comprises means for directing the rinsing solution from the vessel into the respective reagent input mechanism and thence to the sample inlet section and measurement section.

6. Apparatus according to claim 1 further comprising a liquid waste vessel and wherein the analyzer further comprises means for discharging fluids from the measurement chamber and depositing the liquids in said liquid waste vessel through a waste outlet, said analyzer further comprising support means for removably supporting the waste vessel on the analyzer.

7. Apparatus according to claim 6 in which the liquid waste vessel comprises a bottle and a cap permanently attached to the bottle opening, the cap having an aperture, means for selectively opening and closing the aperture and means for co-operating with the waste outlet of the analyzer such that waste liquid directed through the analyzer waste outlet enters the waste vessel through the opened aperture.

8. Apparatus according to claim 1, in which the analyzer is constructed so that when said reagent liquid storage vessel is mounted on the analyzer, the presence of liquid between the outside of the vessel and the analyzer is minimized by providing a protrusion on one or both of a surface of said vessel and a surface of said analyzer, said surfaces being adjacent to each other, said protrusion or protrusions maintaining a distance between said respective surfaces sufficient to prevent capillary formation.

9. Apparatus according to claim 1 wherein the reagent liquid storage vessel fits into one or more cavities in the analyzer, so that the back and bottom of the vessel is surrounded, and the presence of liquid on the lowermost surface of the cavity is minimized by constructing the lowermost surface of the analyzer cavity to incline to the horizontal downwards towards the opening of the cavity such that liquid will run off said lowermost surface.

10. Apparatus according to claim 9, wherein the reagent liquid storage vessel is shaped to correspond to the shape of one or more cavities in the analyzer, by having an inclined lower surface.

11. Apparatus according to claim 1 which the support means for supporting the vessel comprise a pair of rods which are parallel with one another and at substantially the same height and which are secured to the analyzer such that they extend outwardly from the analyzer and the vessel has co-operating means on its two sides for co-operation with the rods, the co-operating means comprising a shoulder at the top of each side of the vessel, each of which rests on one of the rods when the vessel is supported on the analyzer.

12. Apparatus according to claim 11 in which the tube of the analyzer input mechanism is fixed to extend substantially horizontally from the analyzer, and the outlet aperture of the reagent vessel is conveniently arranged to be in a substantially vertical plane as the vessel is mounted on the analyzer.

13. Apparatus according to claim 1 wherein said measurement section comprises electrochemical measuring devices.

14. Apparatus according to claim 13, wherein said electrochemical measuring devices are selected from the group consisting of pH electrodes, $pCO_2$ electrodes, $pO_2$ electrodes, and ion selective electrodes.

15. Apparatus according to claim 13 wherein said measurement section further comprises a photometric sensing device.

16. Apparatus according to claim 15, wherein said measurement section further comprises a photometric sensing device for measuring Hb levels.

17. Apparatus according to claim 1 wherein said liquid reagent storage vessel contains a liquid reagent and comprises a bottle with a cap permanently fixed by a fluid tight fixture to the bottle opening, the cap comprising a cavity having a vertical face which has a sealed outlet aperture in fluid communication with the cavity and capable of being broken by the inlet tube of the input mechanism of said analyzer for conducting measurements of properties of samples of physiological fluids, the cap further comprising an inlet aperture opening into the cavity and being in fluid communication with a reagent liquid conduit which extends into the liquid in the vessel.

18. Apparatus according to claim 17 in which said cap is formed such that the input mechanism of the analyzer is capable of forming a fluid tight communication with the inlet aperture by the provision of a gasket in the cap which seals the connection between the analyzer inlet tube and the liquid conduit in the vessel.

19. Apparatus according to claim 17 wherein said vessel contains all of the components of a rinsing solution.

20. Apparatus according to claim 19 which comprises a base solution contained in the bottle and a proteolytic enzyme in the form of a dry composition isolated from the solution in a form such that the enzyme can be contacted with the base solution and dissolved in it to form the rinsing solution.

21. Apparatus according to claim 20, wherein the proteolytic enzyme is isolated by storing it in a second cavity in the cap of the vessel, the vessel having a seal separating the proteolytic enzyme in the second cavity from the base solution in the bottle, said cap having means for breaking the seal and thereby releasing the enzyme into the base solution.

22. Apparatus according to claim 17, wherein said liquid reagent comprises potassium chloride in solution.

23. Apparatus according to claim 17 which contains a calibrating solution for an analyzer for conducting measurements of properties of samples of physiological fluids.

* * * * *

UNITED STATES PATENT AND TRADEMARK OFFICE
CERTIFICATE OF CORRECTION

PATENT NO. : 5,309,775

DATED : May 10, 1994

INVENTOR(S): Joergen Anderson

It is certified that error appears in the above-identified patent and that said Letters Patent is hereby corrected as shown below:

Column 13:
Claim 11, Line 1: Insert --in-- after "claim 1".

Column 14:
Claim 20, Line 1: Delete "which" and insert --wherein said vessel-- after "claim 19".

Column 14:
Claim 23, line 1: Delete "which" and insert --wherein said vessel-- after "claim 17".

Signed and Sealed this

Twenty-second Day of November, 1994

Attest:

BRUCE LEHMAN

Attesting Officer

Commissioner of Patents and Trademarks